(12) United States Patent
Barbknecht

(10) Patent No.: US 8,696,726 B2
(45) Date of Patent: Apr. 15, 2014

(54) FLEXIBLE CLOSED FLAT PAD FOR COOLING A BODY PART

(75) Inventor: Ingrid Barbknecht, Schwalmtal (DE)

(73) Assignees: SOVIKA GmbH, Jesewitz (DE); Ingrid Barbknecht, Schwalmtal (DE)

( * ) Notice: Subject to any disclaimer, the term of this patent is extended or adjusted under 35 U.S.C. 154(b) by 542 days.

(21) Appl. No.: 12/451,651

(22) PCT Filed: Apr. 29, 2008

(86) PCT No.: PCT/EP2008/003441
§ 371 (c)(1),
(2), (4) Date: Nov. 23, 2009

(87) PCT Pub. No.: WO2008/145238
PCT Pub. Date: Dec. 4, 2008

(65) Prior Publication Data
US 2010/0168825 A1    Jul. 1, 2010

(30) Foreign Application Priority Data
May 25, 2007 (DE) .................... 20 2007 007 570 U

(51) Int. Cl.
*A61F 7/12* (2006.01)

(52) U.S. Cl.
USPC ........................................................ 607/109

(58) Field of Classification Search
USPC ................................................ 607/108, 109
See application file for complete search history.

(56) References Cited

U.S. PATENT DOCUMENTS

| | | | |
|---|---|---|---|
| 3,995,621 A | 12/1976 | Fletcher et al. | |
| 4,753,241 A | 6/1988 | Brannigan et al. | |
| 5,395,399 A | 3/1995 | Rosenwald | |
| 5,597,577 A | 1/1997 | Mathewson | |
| 5,897,581 A * | 4/1999 | Fronda et al. | 607/109 |
| 6,117,164 A | 9/2000 | Gildersleeve et al. | |
| 6,277,143 B1 * | 8/2001 | Klatz et al. | 607/104 |
| 6,500,200 B1 * | 12/2002 | Kushnir | 607/104 |
| 2003/0079488 A1 | 5/2003 | Bieberich | |
| 2004/0210288 A1 | 10/2004 | Karapetyan | |
| 2005/0107856 A1 | 5/2005 | Gammons | |

FOREIGN PATENT DOCUMENTS

| | | | | |
|---|---|---|---|---|
| CA | 2135966 A | * | 5/1996 | ............... A61F 7/10 |
| DE | 3902233 | | 8/1990 | |
| FR | 2742642 | | 6/1997 | |
| FR | 2742642 A1 | * | 6/1997 | ............ A47C 21/04 |
| WO | WO92/13506 | | 8/1992 | |
| WO | 2004071362 | | 8/2004 | |
| WO | WO2005/007060 A2 | | 1/2005 | |
| WO | WO2005/074846 A1 | | 8/2005 | |

* cited by examiner

*Primary Examiner* — Linda Dvorak
*Assistant Examiner* — Jared W Pike
(74) *Attorney, Agent, or Firm* — Price Heneveld LLP

(57) ABSTRACT

An apparatus for cooling a body part includes a flat and flexible closed container defining an interior volume with a plurality of interconnected chambers. An attachment member is connected with the container and is configured for removably attaching the apparatus to a body part. A superabsorber is disposed in the chambers, and the chambers are shaped to be filled with water.

19 Claims, 5 Drawing Sheets

FLEXIBLE CLOSED FLAT PAD FOR COOLING A BODY PART

CLAIM OF PRIORITY

Applicant hereby claims the priority benefits under the provisions of 35 U.S.C. §119, basing said claim of priority on German Utility Model Serial No. 20 2007 007 570.7, filed May 25, 2007. In accordance with the provisions of 35 U.S.C. §119 and Rule 55(b), a certified copy of the above-listed German Utility Model will be filed before grant of a patent.

BACKGROUND OF THE INVENTION

The present invention relates to a device for holding a coolant for cooling a body part. The preferred field of application of the device is the cooling of a human head, implementable by a layman and/or a first aid provider.

Active cooling systems and passive cooling are known in the field of head cooling systems. In the case of active cooling systems, use is made of a head hood with water cooling by a tube system or air cooling. In the case of air cooling, a continuously cooled air stream is guided around the region of the head and the brain is consequently cooled. Passive cooling is typically effected by ice, water evaporation, cool packs and the like.

Until now, active cooling systems for the head have only been applied in clinical situations.

Due to the fact that particularly in the first minutes of oxygen deficiency in the brain thousands of brain cells die and severe life-threatening symptoms develop for the affected party, it is important to drastically minimize the mass death of brain cells.

This is effected by reducing the oxygen use in the brain cells by selectively reducing the temperature in the head as soon as possible whilst maintaining the body temperature as much as possible.

SUMMARY OF THE INVENTION

One object of the present invention is to create a device for holding a coolant for cooling a body part which has a particularly simple design and can be used in an uncomplicated fashion after receiving the coolant.

The invention provides a device for holding a coolant for cooling a body part, wherein the device has a flat and flexible design with a plurality of interconnected chambers, and an attachment member for attaching the device to the body part.

Thus, in principle, the device according to the present invention can be attached to any body part that needs to be cooled. However, the preferred field of application of the device is for cooling the head.

The device according to the present invention in this case relates to the structural configuration of the container before receiving the coolant therein. This structural configuration is generally sold in this condition to save space, and is subsequently filled with the coolant by the purchaser.

For reasons of improved clarity, the following description relates to the function of the device after the same has been filled with a coolant.

The device according to the present invention has a flat and flexible design, such that it and the coolant held thereby can be matched or conformed to the shape of the respective body part to be cooled. A plurality of interconnected chambers affords the possibility of the coolant being freely displaced within the device in accordance with the prescribed contour of the body part. The attachment mechanism is used to attach the device to the body part.

It is considered to be particularly advantageous if the device is prefilled with a powder which has the property of absorbing liquid many times its own weight. Such a powder is also referred to as a superabsorber (superabsorbent polymer, SAP) and is suitable for absorbing liquid, usually water, up to one thousand times its own weight. Then, it is only necessary to add water or the like to the chambers in order to bring about the functionality of the cooling device. According to this feature, in a preferred embodiment of the present invention, the device is provided with a sealable opening for filling the chambers. In particular, the sealable opening can be designed as an armband valve, in the nature of the type of resealable mechanical valve used on a swim ring that is placed around the arm of a child, wherein the swim ring can be inflated.

It is considered to be particularly advantageous if the device which holds the coolant is made from a foil, in particular a plastic foil. Vapor preferably passes through the foil to the outside of the device. The patient feels a pleasant cool temperature on the surface of the device due to this evaporation property. It follows that the sealable opening can also be used to refill the device with liquid due to the evaporation of the liquid within the chambers.

With respect to the container or device which holds the coolant, provision is preferably made for the device to be stored in a refrigerator, not in a freezer, so that the coolant, possibly in the form of a superabsorber/water mixture, is always present in a liquid or gel-like state. This occurs at a temperature below 12° Celsius. As a result of the device and coolant being in this temperature range, harm to the patient as a result of hypothermia, particularly due to the application of ice used in the prior art, is avoided. The chamber volume of the device is sufficiently large for ensuring that the body part of the patient is cooled until the rescue team arrives. This cooling effect lasts for at least 30 minutes.

In accordance with a particular embodiment of the present invention, the device is designed as a flat, flexible pad. This design affords the possibility of producing the pad in a simple and cost-effective manner. The pad is preferably rectangular, and in particular square. In the simplest design thereof, the pad is formed by a foil which has two foil sections folded onto each other, hence a foil which is formed by folding back one foil section onto the other foil section. This arrangement of the foil sections affords the possibility of producing the pad by welding the foil sections to each other in the region of three free sides of the pad. No welding procedure is required in the region of the fourth side because in the folded over region, the foil sections are already interconnected.

The chambers of the pad can be formed very easily by connecting the two pad main walls, which in the illustrated embodiment are the two foil sections folded onto each other. The connection is effected in the region of many points or many short webs. It follows that a plurality or multiplicity of individual chambers of the pad result, wherein the adjacent chambers are closed only at the various point connections or short web connections. It follows that the coolant can arbitrarily or freely flow from one chamber into the adjacent chambers without being restricted in respect of the flow direction of long webs when the device is filled with the coolant and when pressure is exerted onto the pad main wall in certain areas of the pad main wall. The free flow of the coolant within the device ensured by the present invention makes possible optimal matching or shaping of the device to the contour of the respective body part.

So as to be able to conform or match the device, in particular the pad, to the body part in an optimal fashion, the device or the pad is provided with at least one slit on at least one side, and in particular with multiple slits facing one another on opposite sides of the pad. The slits also have the advantage of being able to fold away certain regions of the device or the pad in order to enable the rescue team to access the patient, for example access for a central vein catheter in the folded away region of the pad.

The attachment mechanism for attaching the device to the body part is preferably designed as straps, in particular flat straps. By way of example, the straps can be foil straps or hook and loop straps. These straps permit a largely arbitrary arrangement of the device on the body part to be cooled. In particular, attaching the device provided with coolant on the head in the style of a hood can be realized in an uncomplicated fashion using the straps.

In accordance with a preferred embodiment of the invention, provision is made for the device to be provided with temperature sensors for detecting the surface temperature of the device and/or the temperature of the coolant. Hence, the device not only cools the body part, but the temperature sensors also permit monitoring of the cooling behavior of the device, either continuously or at intervals.

When the device is filled with cold coolant, it lowers the temperature of the body part, particularly in the head, as soon as possible, whilst largely maintaining the body temperature. The device can be used for a wide variety of body parts and is adaptable for all head sizes. It is easy to handle and can be made available in many places, e.g., in the household, in a vehicle, in companies and in public institutions. Due to the cooling range of the device, no harm to the patient is caused as a result of its application. Sufficient cooling is ensured until the arrival of the rescue team. The device conveys a pleasant skin feeling to the patient, particularly when cooling the head of a bald patient, with the result being that defensive behavior and excitation of the affected party are avoided. Furthermore, the device permits soft support of the body part, in particular the head, in order to avoid subsequent damage to the skin, in particular at pressure points and impact injuries. The simple design of the device allows cost-effective production thereof, as a result of which the device can readily have a broad application for care in the population. As a result of the flat form of the device, it can easily be modulated around the body part, in particular the head, and subsequently be attached to the body part using the attachment mechanism. If the coolant is a water/gel mixture, filling the device therewith is relatively simple, particularly if the device is delivered already filled with the gel, and hence only water has to be introduced into the device. For the corresponding heat exchange, a high water content is to be strived for.

Further preferred fields of application of the device filled with the coolant are support aids for decubitus prophylaxis, the cooling of extremities or other regions in the case of local heating (e.g., as a result of inflammation) and the stabilized support of extremities.

Additional features of the invention are disclosed in the following description of the drawings, the drawings themselves and in the dependent claims.

BRIEF DESCRIPTION OF THE DRAWINGS

In the drawings, the invention is illustrated on the basis of two preferred exemplary embodiments, without being restricted to these.

DETAILED DESCRIPTION OF THE PREFERRED EMBODIMENTS

Figure 1:
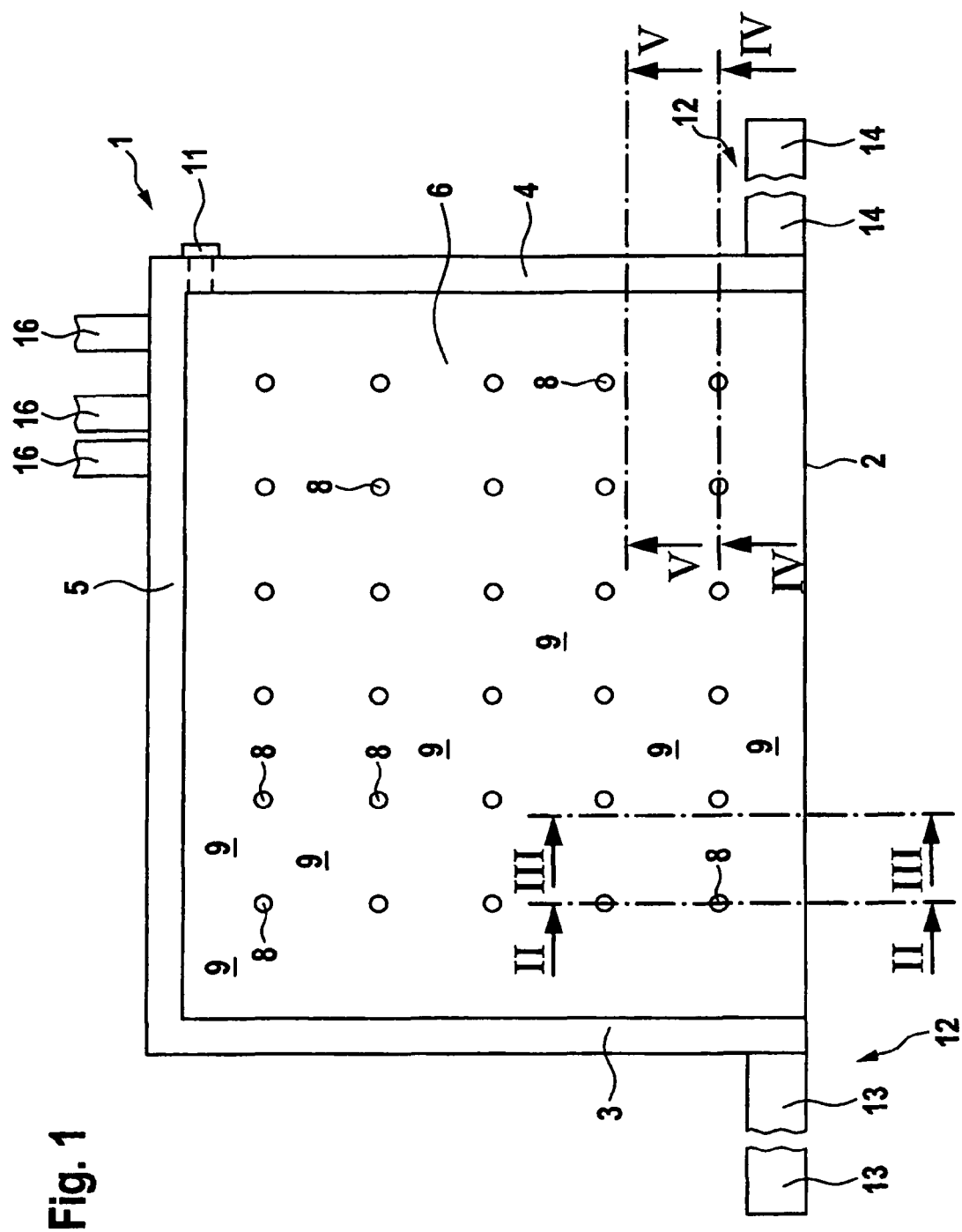
FIG. 1 shows a view of the device formed as a pad for holding the coolant for cooling a body part, seen in the direction of the main face of the pad which faces the body part when the device is placed onto the body part.
Figure 2:
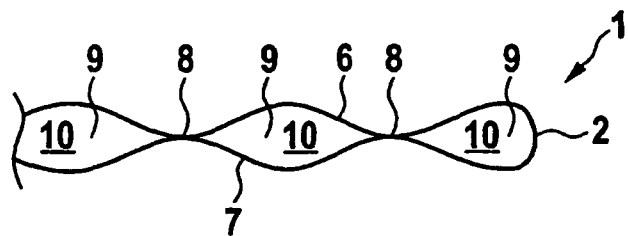
FIG. 2 shows a cross section through the device filled with coolant taken along the line II-II in FIG. 1.
Figure 3:
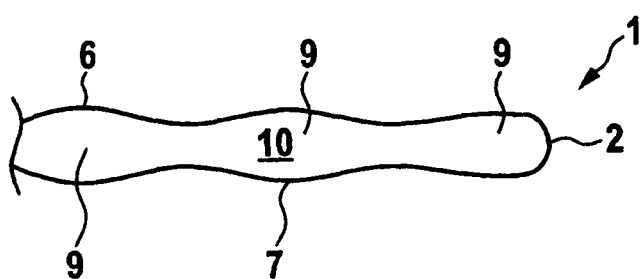
FIG. 3 shows a cross section through the device filled with coolant taken along the line III-III in FIG. 1.
Figure 4:
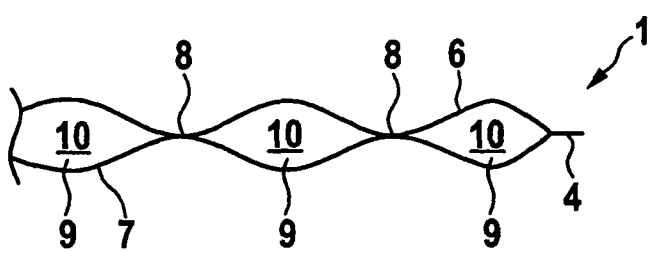
FIG. 4 shows a cross section through the device filled with coolant taken along the line IV-IV in FIG. 1.
Figure 5:
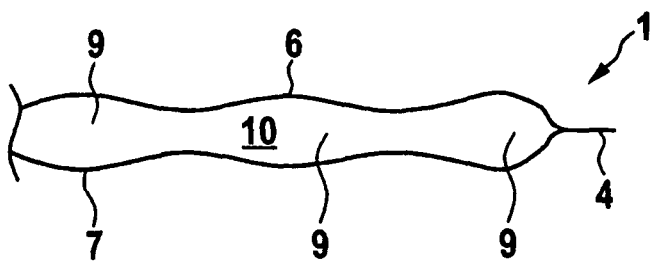
FIG. 5 shows a cross section through the device filled with coolant taken along the line V-V in FIG. 1.
Figure 6:
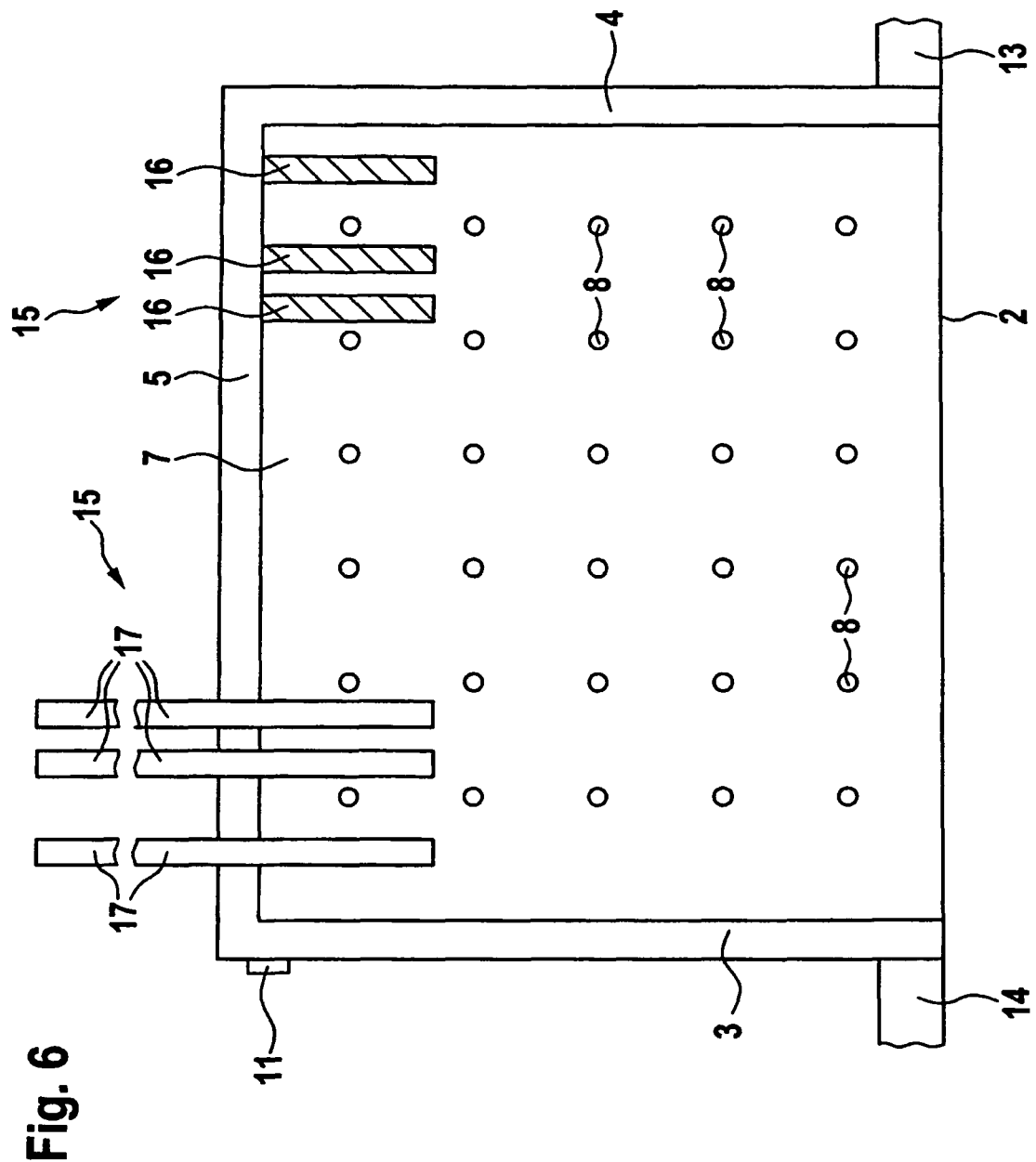
FIG. 6 shows a view of the device illustrated in FIG. 1, seen in the direction of the main face of the pad which faces away from the body part when the device is placed onto the body part.

For purposes of description herein, the terms "upper", "lower", "right", "left", "rear", "front", "vertical", "horizontal" and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The first illustrated embodiment of the device 1 according to the present invention for holding a coolant is shown in FIGS. 1-7, and consists of a breathable polyurethane foil with an initial size of approximately 100 cm×50 cm. This foil is arranged in two layers, resulting in a flat square plan shape, with the dimensions of approximately 50 cm×50 cm. The folded over or bending edge of the foil is referred to by the reference numeral 2. In the region of the three other edges, the foil boundaries are welded together, and the two parallel foil boundaries are referred to by the reference numerals 3 and 4, and the foil boundary running parallel to the bending edge 2 is referred to by the reference numeral 5. This results in a closed pad volume with the pad main faces 6 and 7 arranged between the bending edge 2 and the foil boundaries 3-5, wherein the pad main face 6 faces the body part to be cooled during use, and the pad main face 7 faces away from the body part to be cooled during use of the pad. The two pad main faces 6 and 7 are interconnected by a plurality of spot welds, specifically with a point grid with thirty-six welding spots 8 for connecting the pad main faces 6 and 7, wherein six rows of respectively six welding spots 8 are formed. The point grid formed by the thirty-six welding spots 8 has the outer contour of a square which runs symmetrically with respect to the outer contour of the pad.

As a result of the various welding spots 8, the interior volume of the device 1 or the pad is subdivided into a plurality or multiplicity of chambers 9, as can be seen from the various sectional illustrations in accordance with FIGS. 2-5.

In these sectional illustrations, the device 1 with coolant 10 contained therein is shown. In this case, this is a mixture of water, e.g., an amount of two to three liters of water, and a superabsorber, e.g., ten to twelve grams of the superabsorber. Thus, in this case the coolant 10 presents itself as a gel-like mass which can easily be displaced within the pad, in particular displaced between the chambers 9, as a result of pressure acting on the pad main faces 6 and 7.

A sealable inlet valve 11 is provided for filling the pad 1. The device 1 is delivered filled only with the superabsorber. The user then fills the device 1 with water through the sealable inlet valve 11. After sealing the inlet valve 11, the pad 1 is placed in a refrigerator or transport cold box and is stored at approximately +5° Celsius. Hence, the pad is always ready for use at the mentioned temperature and then only has to be removed from the refrigerator or the transport cold box.

The pad 1 has various attachment mechanisms for positioning it on a body part, particularly a human body part. A first attachment element 12 is, for example, designed as a hook and loop fastener, and has a fleece strap 13 connected to the foil boundary 3 in the region of the bending edge 2, and a hook strap 14 connected to the foil boundary 4 in the region of the bending edge 2. The fleece strap 13 and hook strap 14 can have various lengths. These two straps 13 and 14 run along and parallel with the longitudinal extent of the bending edge 2 in a loosely laid out state.

A second attachment element 15, which likewise is a hook and loop fastener, is connected to the pad 1 in the region of the foil boundary 5. The second attachment element 15 has three hook straps 16 which are arranged parallel to the foil boundary 3, approximately in the region of the third of the pad associated with this foil boundary 3, and extend over approximately a third of the length of the foil boundary 3. Hence, these three hook straps 16 are connected to the pad main face 7, as can be seen in particular in FIG. 6. Three fleece straps 17 are attached to the pad main face 7 adjacent to the foil boundary 3 and in the third of the pad 1 adjacent to the foil boundary 3. The ends of fleece straps 17 protrude over the foil boundary 5 in the initial planar condition of the pad 1, and are oriented parallel to the foil boundaries 3 and 4.

Figure 7:
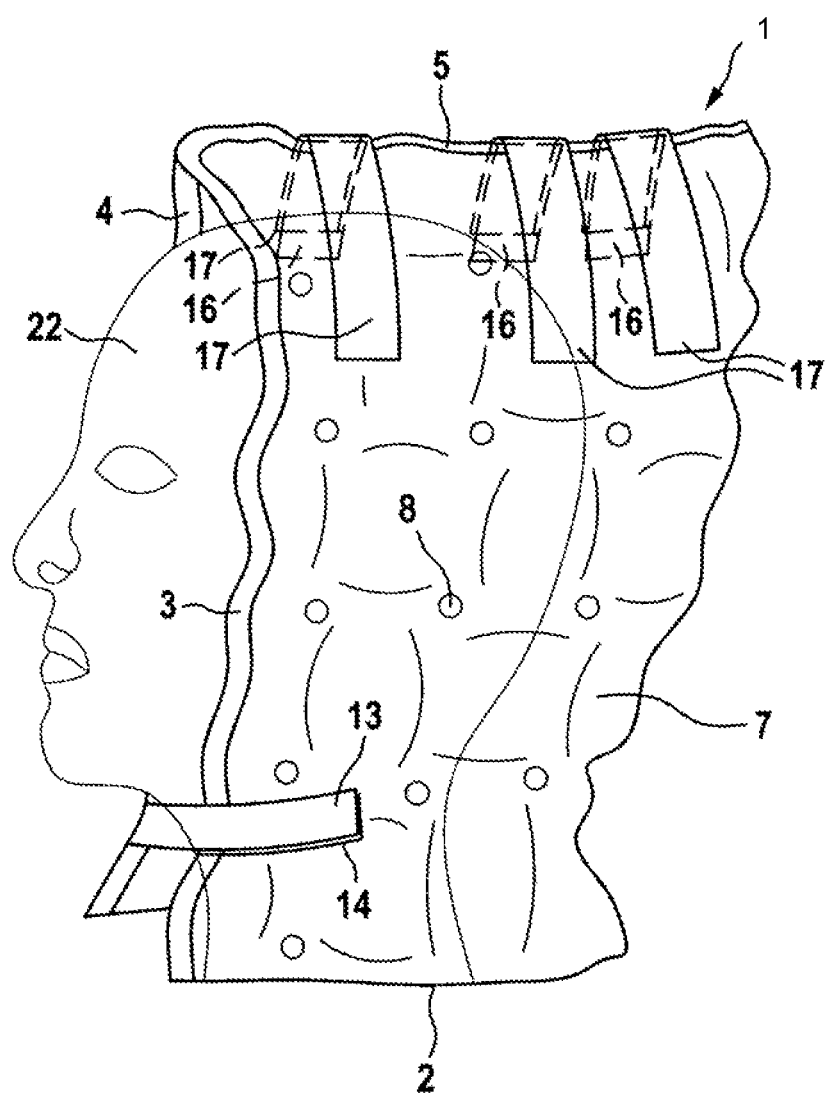
FIG. 7 shows the device of FIGS. 1-6 filled with coolant and attached to a human head.
Figure 8:
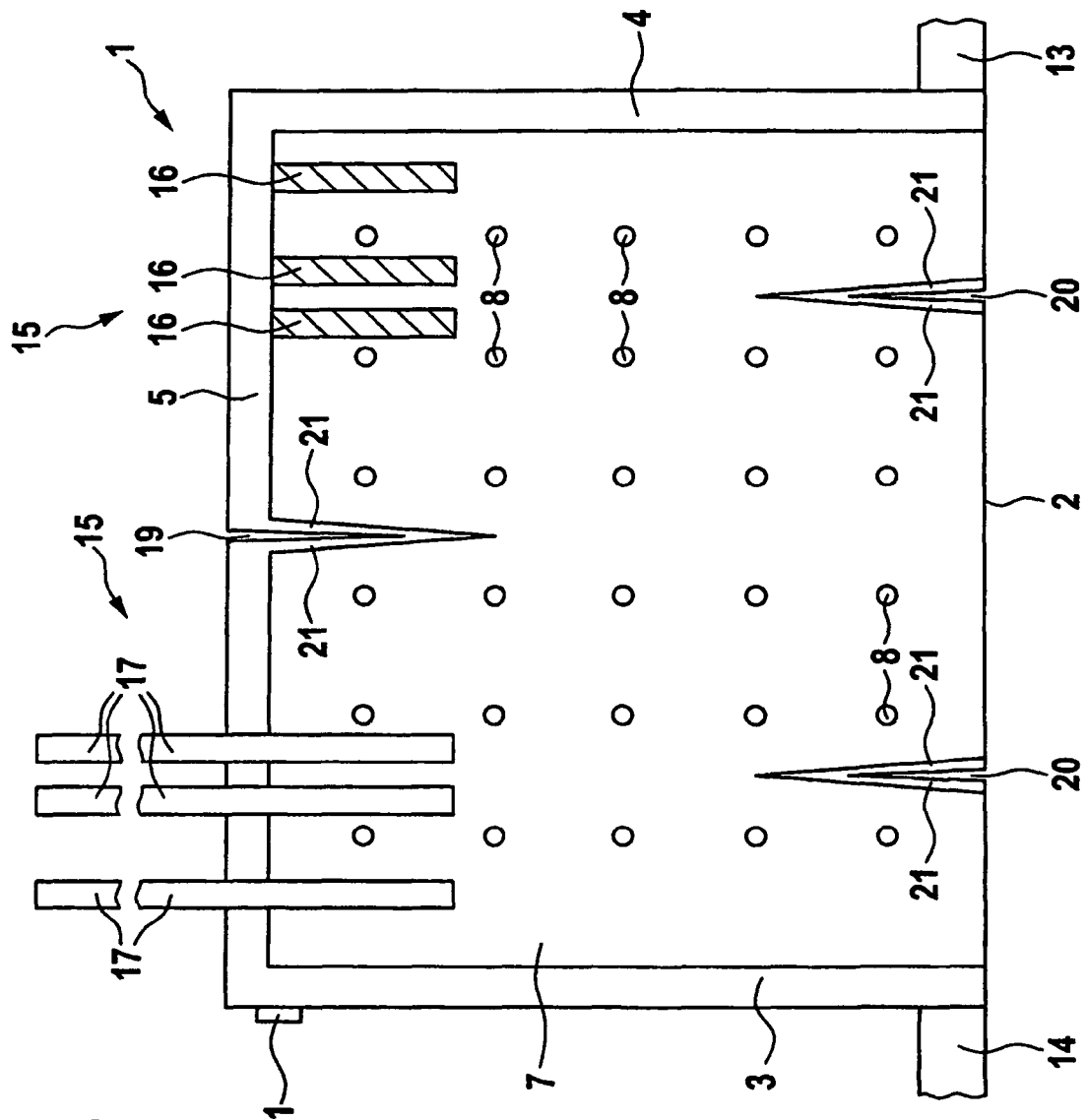
FIG. 8 shows another embodiment of the invention which is similar to the first embodiment of FIGS. 1-7, but is provided with three slits.

The pad 1 can now be placed in the style of a bandana around the head 22 of a patient, as illustrated in FIG. 7. FIG. 7 discloses that, with respect to the orientation of the pad according to FIG. 1, the lower half of the pad rests on the back of the head and to the side of the back of the head. The head hood formed in this fashion is closed in the region of the neck by the fleece strap 13 and the hook strap 14, while the right and left halves of the upper half of the pad 1 are pulled into an overlapping arrangement, as a result of which the hook straps 16 and the fleece straps 17 reach a virtually aligned arrangement with respect to one another. Consequently, the hood 1 can be closed in the region of the cranium by means of the hook straps 16 and the fleece straps 17.

Compared to the embodiment according to FIGS. 1 to 7, FIG. 8 shows a slightly modified design of the pad 1. It only differs in that, in the region of the foil boundary 5, provision is made in the pad for a single slit 19, which extends toward the bending edge 2, and two slits 20 extending toward the foil boundary 5. Slits 20 extend inwardly from the bending edge 2, and are not arranged centrally, like the slit 19, but rather on the outside portions of the pad 1, adjacent to the respective foil boundaries 3 or 4.

The respective slits 19 and 20 are produced by areal welding of the two pad main faces 6 and 7 in the region of the slits. The respective welding boundaries are noted by the reference numeral 21. The slit 19 permits a particularly precise resting of the pad 1 in the region of the upper cranium of the patient because the regions of the pad adjacent to the slit 19 can be brought into an overlapping arrangement particularly easily, and can be attached by means of the hook strap 16 and the fleece strap 17. The slits 20 are used for uncovering the neck of the patient in an uncomplicated fashion, in particular for applying an external vein access.

The device 1 can additionally be provided with temperature sensors for detecting or acquiring the surface temperature of the pad, specifically the temperature of the pad main face 6 which rests on the body part. If the pad 1 is used as a head hood, additional receptacles can be provided in the pad main face 6 for the insertion of ear protectors in order to avoid too much cooling of the ears of the patient.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The invention claimed is:

1. An emergency medical apparatus for cooling an injured human head, comprising:

a flexible, elastically pliable, closed, plastic layer or film coolant liquid container pad which is folded from an unfolded flat storage configuration into a folded head hood configuration to cover and cool an injured human head, and including:

first and second oppositely disposed, overlying main plastic layer or film walls sealed about a marginal portion thereof to define therebetween an interior volume configured to receive and retain a coolant liquid therein;

said first and second plastic layer or film main walls being laterally interconnected at a plurality of points or webs to define a plurality of interconnected chambers, each configured to receive the coolant liquid therein, and permit the coolant liquid in said pad to flow freely between said chambers to improve close conformance of said pad to an injured human head;

said sealed marginal portion of said pad being defined by an upper edge generally configured to cover a top portion of the injured human head when in said folded head hood configuration, a lower edge generally configured to cover a neck portion of the injured human head when in said folded head hood configuration, and opposite side edges oriented generally perpendicular to said upper and lower edges when in said unfolded flat storage configuration;

at least one sealed slit opening through said upper edge of said marginal portion of said pad and extending toward said lower edge of said marginal portion of said pad when in said unfolded flat storage configuration, and providing said pad with sufficient flexure whereby opposite sides of said upper edge of said pad at opposite areas of said sealed slit assume an overlapped relationship at a location adjacent the upper cranium portion of the injured human head, when in said folded head hood configuration, and conform to the shape of a variety of differently shaped injured human heads, and also provide selective access to portions of the injured human head without requiring complete removal of said pad therefrom;

a resealable mechanical inlet valve in communication with said interior volume of said pad and being manually shiftable between an open condition in which coolant liquid can flow through said inlet valve into said chambers in said pad for filling and refilling said pad with coolant liquid, and a closed condition in which coolant liquid cannot flow through said inlet valve to prevent leakage of the coolant liquid from said pad;

an attachment member connected with said pad, extending between said opposite sides of said upper edge of said sealed marginal portion of said pad and across said sealed slit opening, and removably attaching said apparatus to the injured human head adjacent the top portion thereof when in said folded head hood configuration and selectively retaining said opposite sides of said upper edge in said overlapped relationship; and a super absorber predisposed in said chambers of said pad prior to medical use of said apparatus; and wherein:

said chambers are configured to be filled with liquid water through said inlet valve with said pad in said unfolded flat storage condition prior to medical use, which liquid water is absorbed by said superabsorber predisposed in said chambers of said pad and forms a liquid mixture that is cooled in said unfolded flat storage condition prior to use; and said plastic layer or film is constructed to retain the liquid water and associated liquid mixture in said pad without leakage of the liquid water and associated liquid mixture, yet permit water vapor from the liquid water and associated liquid mixture in said pad to flow through said first and second plastic layer or film main walls, whereby the liquid water in said chambers in said interior volume of said pad evaporates when said pad in said folded head hood configuration is positioned on an injured human head, causing cooling of said pad during medical use, and permits the refilling of said pad with liquid water through said inlet valve to continue evaporative cooling of said pad.

2. An apparatus as set forth in claim 1, wherein:
said first and second pad main walls are interconnected by welding spots or short welding webs.

3. An apparatus as set forth in claim 2, wherein:
said pad has a generally square plan shape wherein in said unfolded flat storage configuration.

4. An apparatus as set forth in claim 3, wherein:
said pad comprises a single sheet of plastic layer or film with two sections folded onto each other and welded together along three adjacent sides of said sealed marginal portion of said pad.

5. An apparatus as set forth in claim 4, wherein:
said pad includes a plurality of said slits arranged facing one another along said upper edge and lower edge of said pad.

6. An apparatus as set forth in claim 5, wherein:
said attachment member comprises a plurality of flat straps.

7. An apparatus as set forth in claim 6, wherein:
said straps comprise plastic layer or film straps or hook and loop straps.

8. An apparatus as set forth in claim 7, wherein:
said attachment member defines a first attachment member comprising a plurality of interacting elements which are spaced apart from each other along said opposite sides of said upper edge of said pad and extend outwardly therefrom.

9. An apparatus as set forth in claim 8, including:
a second attachment member connected with said pad, extending between said side edges of said sealed marginal portion of said pad, and configured for removably attaching said apparatus to the injured human head adjacent the neck portion thereof in said folded head hood configuration.

10. An apparatus as set forth in claim 9, wherein:
said second attachment mechanism comprising a plurality of second interacting elements disposed adjacent said lower edge of said pad and extending outwardly in opposite directions therefrom.

11. An apparatus as set forth in claim 10, wherein:
one of said first and second attachment members comprises a fleece strap and a hook strap configured to interact with said fleece strap.

12. An apparatus as set forth in claim 1, wherein:
said pad has a generally square plan shape when in said unfolded flat storage configuration.

13. An apparatus as set forth in claim 1, wherein:
said pad comprises a single sheet of plastic layer or film with two sections folded onto each other and welded together along three adjacent sides of said sealed marginal portion of said pad.

14. An apparatus as set forth in claim 1, wherein:
said pad includes a plurality of said slits arranged facing one another along said upper edge and lower edge of said pad.

15. An apparatus as set forth in claim 1, wherein:
said attachment member comprises a plurality of flat straps.

16. An apparatus as set forth in claim 15, wherein:
said straps comprise plastic layer or film straps or hook and loop straps.

17. An apparatus as set forth in claim 1, wherein:
said attachment member defines a first attachment member comprising a plurality of interacting elements which are spaced apart from each other along said opposite sides of said upper edge of said pad and extend outwardly therefrom.

18. An apparatus as set forth in claim 1, including:
a second attachment member connected with said pad, extending between said side edges of said sealed marginal portion of said pad, and configured for removably attaching said apparatus to the injured human head adjacent the neck portion thereof in said folded head hood configuration.

19. An apparatus as set forth in claim 18, wherein:
said second attachment mechanism comprising a plurality of second interacting elements disposed adjacent said lower edge of said pad and extending outwardly in opposite directions therefrom.

* * * * *